United States Patent [19]

Ose

[11] 4,283,388
[45] Aug. 11, 1981

[54] METHOD FOR TREATING COLIBACILLOSIS IN PIGS WITH TYLOSIN APRAMYCIN COMPOSITIONS

[75] Inventor: Earl E. Ose, Greenfield, Ind.

[73] Assignee: Eli Lilly and Company, Indianapolis, Ind.

[21] Appl. No.: 107,240

[22] Filed: Dec. 26, 1979

[51] Int. Cl.³ .............................................. A61K 35/00
[52] U.S. Cl. ..................................................... 424/114
[58] Field of Search ......................................... 424/114

[56] References Cited

U.S. PATENT DOCUMENTS

| 3,178,341 | 4/1965 | Hamill et al. | 424/121 |
| 3,876,767 | 4/1975 | Ose | 424/116 |

OTHER PUBLICATIONS

Ose, Veterinary Medicine/Small Animal Clinician, vol. 71, No. 1, pp. 92–95, Jan. 1976.
Ose, Veterinary Medicine/Small Animal Clinician, vol. 68, No. 5, pp. 539–543, May 1973.
The Merck Veterinary Manual, 5th Ed., pp. 153–154, 174–175, 293–303 & 504, Merck & Co., Inc., Rahway, N.J. (1979).
Handbook of Veterinary Drugs, pp. 628–629, Springer Publishing Co., N.Y., 1974.
Chemical Abstracts 80:63778g (1974).

Primary Examiner—Jerome D. Goldberg
Attorney, Agent, or Firm—William B. Scanlon; Arthur R. Whale

[57] ABSTRACT

Antibiotic compositions comprising tylosin and apramycin are effective in the treatment and control of colibacillosis in weanling pigs, and demonstrate greater effectiveness than apramycin alone or tylosin alone.

11 Claims, 1 Drawing Figure

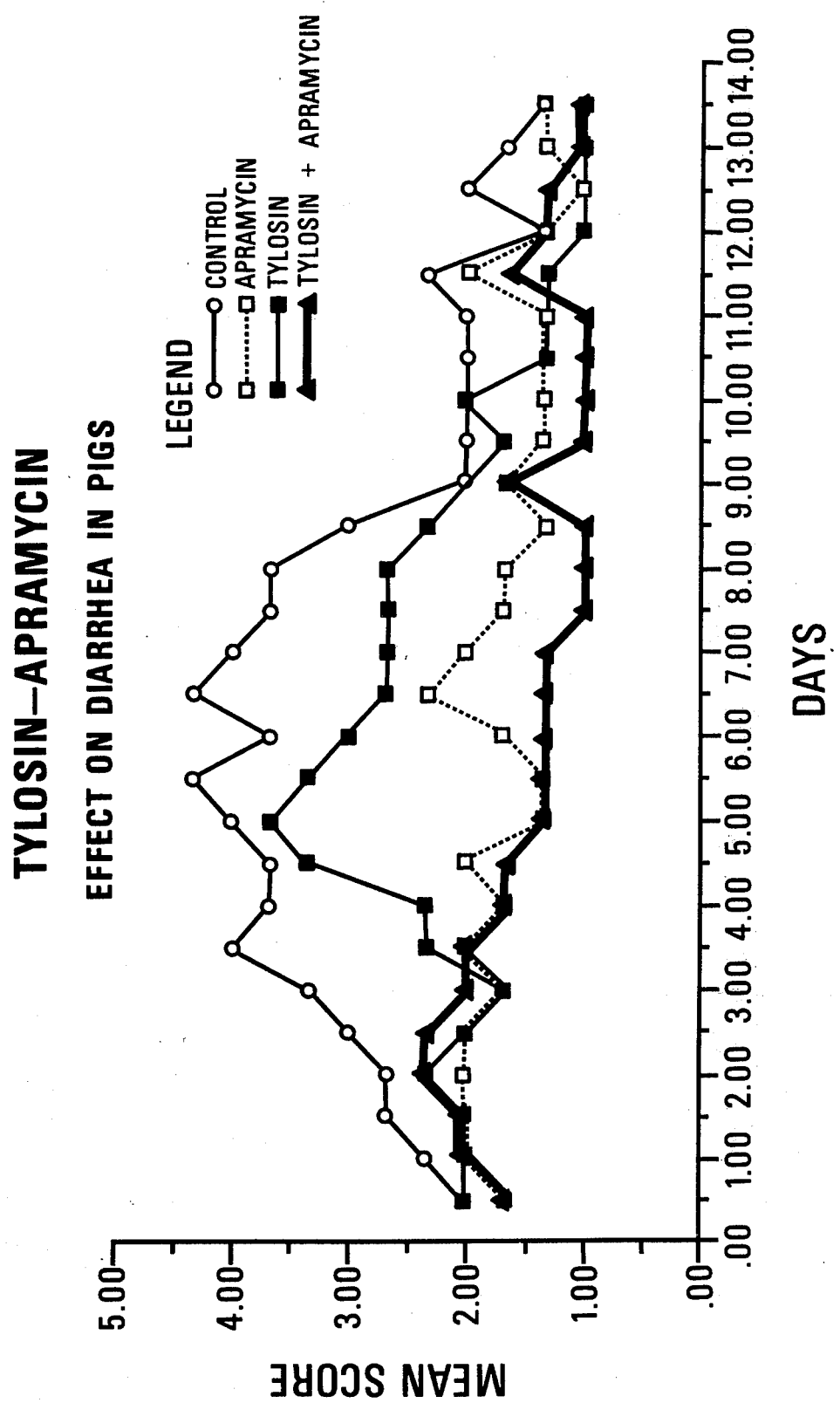

METHOD FOR TREATING COLIBACILLOSIS IN PIGS WITH TYLOSIN APRAMYCIN COMPOSITIONS

SUMMARY

Antibiotic compositions comprising the combination of tylosin and apramycin are useful in the treatment and control of colibacillosis in weanling pigs. The combination of the two antibiotics exhibits greater reduction in the incidence of diarrhea, higher weight gains and feed efficiency than either antibiotic administered alone. The tylosin-apramycin composition can be administered in the animal feed or drinking water and can be formulated in commonly used premix formulations.

BACKGROUND OF THE INVENTION

This invention relates to the use of antibiotics in veterinary medicine. In particular it relates to a method for the treatment and control of colibacillosis in weanling pigs with an antibiotic composition comprising tylosin and apramycin.

Colibacillosis in a common disease in weaned pigs which can result in economic loss to the animal raiser. The disease is caused by enterotoxigenic strains of the gram-negative microorganism *Escherichia coli* and results in poor performance by the pigs. Specifically the pigs fail to gain weight, experience diarrhea, feed efficiency is decreased and mortalities may occur. As a result there is a delay in normal growth for some weeks.

Tylosin has long been used as an antibacterial in veterinary medicine. The antibiotic has been used to control mycoplasma infections in poultry, as a growth promoter for pigs, and in the treatment and control of swine dysentery. However, tylosin is not known to be useful in the treatment and control of colibacillosis in post weaned pigs.

Apramycin is a highly effective antibiotic recently put to use in veterinary medicine. Apramycin, previously known as nebramycin factor II, is described in U.S. Pat. No. 3,691,279. U.S. Pat. No. 3,876,767 claims and describes the use of apramycin in promoting the growth of swine as well as its use in the treatment and control of swine dysentery and salmonellosis.

DETAILED DESCRIPTION

The antibiotic composition employed in the method of this invention is highly effective in reducing the severity of colibacillosis which occurs following weaning in pigs. According to the method of this invention the administration of compositions comprising tylosin-apramycin to weanling pigs reduces the incidence of diarrhea to a significantly greater extent than that observed following the administration of either antibiotic alone. The compositions also increase weight gain and result in improved feed efficiency to an extent greater than with either component alone.

In practicing the present invention the two antibiotics can be mixed at a suitable level in the pigs feed or alternatively they can be administered in the animal's drinking water at suitable concentrations.

The efficacy of the tylosin-apramycin combination was demonstrated in controlled studies in weanling pigs. The results show that pigs treated with the antibiotic combination had a significantly greater reduction in the incidence of *E. coli* diarrhea than did the pigs treated with apramycin alone or with tylosin alone. Further the pigs treated with the antibiotic compositions showed higher average daily weight gains and greater improved feed efficiency than did pigs treated with either antibiotic alone.

The following Table 1 shows the results obtained in a 21 day study with weanling pigs. Tylosin and apramycin were each administered in the feed at a level of 110 ppm. The antibiotic combination was likewise administered in the feed containing both antibiotics at the 110 ppm level. The results are shown as a percentage increase over a non-treated control group as calculated from the statistical evaluation of the data obtained in the study.

TABLE 1

| Treatment | Percent Increase Over Controls | | |
|---|---|---|---|
| | Average Daily Weight Gain | Improved Feed Efficiency | Reduction of Diarrhea |
| Apramycin | 19.0 | 10.3 | 42.8 |
| Tylosin | 29.7 | 11.4 | 26.4 |
| Tylosin/Apramycin | 40.6 | 16.1 | 48.7 |

As shown in Table 1 tylosin when used alone was effective in improving feed efficiency, weight gain and in reducing the incidence of diarrhea. Apramycin when used alone likewise showed its known effectiveness in each category. Surprisingly, the use of both antibiotics in combination showed greater improvement in each category than did the use of apramycin alone. As noted above, tylosin was not previously known to be effective in the treatment of colibacillosis in post weaned pigs and, consequently the greater effectiveness of the tylosin-apramycin combination over that displayed by apramycin was unexpected.

The method of this invention comprises administering to weanling pigs a therapeutically effective amount of tylosin and apramycin. The total amount of both antibiotics as well as the proportionate amounts of each which may be administered can vary. The effective concentration of the antibiotics in the animal's feed can depend on such factors as the severity of the disease, and the age and weight of the animals. The concentration of both antibiotics together in the feed can be between about 50 ppm and about 1000 ppm with the ratio by weight of tylosin to apramycin of from about 5:1 to about 1:5. A generally useful concentration of both antibiotics together in feed is between about 100 ppm and about 300 ppm. A preferred concentration is about 220 ppm with a ratio by weight of the antibiotics of 1:1.

Tylosin and apramycin are basic substances which form salts with mineral acids, carboxylic acids and sulfonic acids such as the hydrochloride, sulfate, phosphate, tartrate, citrate, laurylsulfate, hexanoate, benzenesulfonate, and like salts. The salt form of the antibiotics as well as the free base form can be employed in the method of this invention. Preferred salts of tylosin are the tartrate and the phosphate salts. Preferred salts of apramycin are the sulfate and hydrochloride salts.

The tylosin and apramycin can be formulated together in a premix or in separate premixes for mixing with the final feed. Alternatively, the two antibiotics can be mixed directly into the final feed.

The antibiotics in the base form are appreciably soluble in water as are the salts of the antibiotics. The antibiotics and preferably the salt forms thereof can be added to the animal's drinking water to form solutions at therapeutically effective concentrations. As with the concentration in the animal's feed the concentration of the antibiotics in drinking water may be varied. Concentrations of both antibiotics of between about 10 mcg/ml to about 500 mcg/ml, with a ratio of the antibiotics by weight of about 5:1 to 1:5, are generally sufficient to provide control and treatment in the animals. A preferred concentration of the antibiotics in the drinking water is between about 50 mcg/ml to about 300 mcg/ml.

While the antibiotic compositions of tylosin and apramycin are most practically administered in the animal's feed or drinking water the compositions are also effective when injected into the pigs. For administration by injection the two antibiotics can be formulated with a suitable pharmaceutically acceptable diluent such as water, physiological saline or dextrose. The administration of the tylosin-apramycin compositions by injection can be used to treat weanling pigs which are too debilitated by the disease to eat or to consume a sufficient amount of the medicated feed. In such instances the antibiotic compositions can be administered to the pigs by daily injection. Alternatively the antibiotics can be formulated in suitable oral dosage forms, for example in tablets, capsules, or suspensions, and administered to pigs which are incapable of eating a sufficient quantity of the medicated feed.

The efficacy of the tylosin-apramycin combination in the treatment and control of colibacillosis is shown by the results obtained in a 21 day trial with weanling pigs. The pigs were divided by weight into treatment and control groups of eight pigs. Each treatment was randomly assigned to three groups. The animals were fed a normal ration ad libitum with the treatment groups receiving feed containing 110 ppm of each antibiotic. Weight gains, feed efficiency and the incidence of diarrhea were used to measure the response to treatment. The results obtained after 21 days are shown in Table 2.

TABLE 2

TYLOSIN-APRAMYCIN 21 DAY TREATMENT OF WEANLING PIGS

| Treatment[1] | Average Daily gain (kg) | Average Daily Feed (kg) | Feed Efficiency | Diarrhea[2] Index |
|---|---|---|---|---|
| Control | 0.23 | 0.42 | 1.81 | 2.84 |
| Apramycin | 0.29 | 0.47 | 1.64 | 1.64 |
| Tylosin | 0.31 | 0.51 | 1.62 | 2.10 |
| Tylosin/Apramycin | 0.34 | 0.51 | 1.53 | 1.46 |

[1]Tylosin phosphate and apramycin sulfate at 110 ppm in feed. Tylosin-apramycin combination at 110 ppm of each antibiotic in feed.
[2]The diarrhea index was based on the following system with scoring twice daily for the first 13 days and once on the 14th day.
1. Formed stools only.
2. Formed stools, <50% unformed.
3. Unformed stools, >50% unformed.
4. Unformed stools only.
5. Liquid stools only.

The accompanying drawing graphically shows the plot of the mean diarrhea scores vs time in days obtained in the above study. Plotted are the mean scores obtained with the control group and the treated groups. As shown by the plot of the mean scores for the group treated with the tylosin-apramycin combination the incidence of diarrhea was significantly lower than the incidence for the group treated with apramycin along. The graph also shows that tylosin alone was of some effectiveness in reducing the incidence of diarrhea.

In carrying out the method of this invention the weanlings are treated with the antibiotic combination from the time of weaning to 3-4 weeks post-weaning. In the case of severe disease incidence the treatment can be maintained for a longer time if necessary.

The data presented in Table 1 above show the difference in the incidence of diarrhea between the treated groups and the control group expressed as the percentage of the control incidence.

The following Example further illustrates the practice of the method of this invention.

EXAMPLE

Ninety-six weanling pigs averaging 6.0 kg in weight were randomly allocated by weight into 12 pens of 8 pigs per pen. Four treatments were used in the study as follows: (1) Non-medicated controls; (2) apramycin fed at 110 ppm; (3) tylosin phosphate fed at 110 ppm; and (4) apramycin sulfate and tylosin phosphate both fed at 110 ppm. Each treatment was replicated through three pens.

The pigs were fed for 21 days ad libitum a ration of 20% protein corn-soy meal with some rolled oats included for roughage. Vitamins and minerals were added as needed to balance the ration. The only difference in the rations fed to all pigs was the inclusion of the appropriate antibiotic or antibiotic combination in each of the medicated rations. All feed was weighed as fed, with the feed remaining at the end of the weigh period, weighed and discarded. The pigs were weighed at the initiation of the study and weekly thereafter.

Diarrhea scores were maintained on a pen basis. The scoring was done by the same person on a twice daily schedule for the first 13 days and once only on the 14th day. The scoring index was the same as that shown in footnote 2 of Table 2.

An extra pen of pigs was maintained for bacteriological surveys. These pigs were sacrificed as diarrhea was first observed as occurring following allocation of animals to individual pens and prior to the feeding of any medicated rations.

The number of beta hemolytic $E.$ $coli$ per ml of duodenum or ileum contents was determined for the sacrificed animals. The results demonstrated the presence of $E.$ $coli$ at levels of $10^7$ and $10^8$ in the duodenum of the two animals assayed. Negative results were obtained on culturing for salmonella.

The results of the study expressed in weight gain, reduced incidence of diarrhea and improved feed efficiency are shown in Tables 1 and 2 herein.

I claim:

1. A method for treating colibacillosis in post-weanling pigs in need of said treatment which comprises administering to said pigs in an amount effective to treat collibacillosis of an antibiotic composition comprising tylosin and apramycin or physiologically acceptable salts thereof wherein said composition contains a ratio by weight of tylosins to apramycin of about 5:1 to about 1:5.

2. The method of claim 1 wherein the antibiotic composition comprises tylosin phosphate and apramycin sulfate.

3. The method of claim 1 wherein the antibiotic composition is administered in the animal feed.

4. The method of claim 3 wherein the antibiotic composition is present in the feed at a concentration of between about 50 ppm and about 1000 ppm.

5. The method of claim 3 wherein the antibiotic composition is present in the feed at a concentration between about 100 ppm and about 300 ppm.

6. The method of claim 3 wherein the antibiotic composition comprises tylosin phosphate and apramycin sulfate.

7. The method of claim 6 wherein tylosin phosphate and apramycin sulfate are present in about equal concentrations of about 110 ppm.

8. The method of claim 1 wherein the antibiotic composition is administered in the animal drinking water.

9. The method of claim 8 wherein the composition comprises tylosin tartrate and apramycin sulfate.

10. The method of claim 8 wherein the composition is present in the drinking water at a concentration of between about 10 mcg/ml to about 500 mcg/ml.

11. The method of claim 8 wherein the composition is present in the drinking water at a concentration of between about 50 mcg/ml to about 300 mcg/ml.

* * * * *